(12) United States Patent
Chambers et al.

(10) Patent No.: US 6,682,698 B2
(45) Date of Patent: Jan. 27, 2004

(54) APPARATUS FOR EXCHANGING GASES IN A LIQUID

(75) Inventors: Sean D. Chambers, Ann Arbor, MI (US); Jean P. Montoya, Ann Arbor, MI (US)

(73) Assignee: Michigan Critical Care Consultants, Inc., Ann Arbor, MI (US)

( * ) Notice: Subject to any disclaimer, the term of this patent is extended or adjusted under 35 U.S.C. 154(b) by 0 days.

(21) Appl. No.: 09/938,007

(22) Filed: Aug. 23, 2001

(65) Prior Publication Data

US 2003/0039582 A1 Feb. 27, 2003

(51) Int. Cl.$^7$ .......................... A61M 1/14; A61M 37/00
(52) U.S. Cl. .................... 422/45; 422/44; 422/46; 604/6.13; 604/6.14
(58) Field of Search .................. 422/44–46; 604/6.13, 604/6.14, 4.01, 5.01

(56) References Cited

U.S. PATENT DOCUMENTS

| | | | |
|---|---|---|---|
| 3,656,873 A | * | 4/1972 | Schiff ........................ 417/395 |
| 4,374,088 A | | 2/1983 | Stenberg et al. |
| 4,533,516 A | | 8/1985 | Johnsson et al. |
| 4,938,766 A | | 7/1990 | Jarvik |
| 4,986,809 A | | 1/1991 | Hattler |
| 5,034,188 A | | 7/1991 | Nakanishi et al. |
| 5,098,376 A | | 3/1992 | Berry et al. |
| 5,122,113 A | | 6/1992 | Hattler |
| 5,137,531 A | | 8/1992 | Lee et al. |
| 5,167,921 A | | 12/1992 | Gordon |
| 5,230,862 A | | 7/1993 | Berry et al. |
| 5,270,004 A | | 12/1993 | Cosentino et al. |
| 5,270,005 A | | 12/1993 | Raible |
| 5,336,164 A | | 8/1994 | Snider et al. |
| 5,346,621 A | | 9/1994 | Haworth et al. |
| 5,376,334 A | | 12/1994 | Haworth et al. |
| 5,382,407 A | | 1/1995 | Leonard |
| 5,578,267 A | | 11/1996 | Cosentino et al. |
| 5,609,632 A | | 3/1997 | Elgas |
| 5,698,161 A | | 12/1997 | Montoya |
| 5,762,869 A | | 6/1998 | White et al. |
| 5,762,875 A | | 6/1998 | Gremel et al. |
| 5,770,073 A | | 6/1998 | Bach et al. |

(List continued on next page.)

OTHER PUBLICATIONS

Franco L. Fazzalari, et al., "The Development of an Implantable Artificial Lung," ASAIO Journal, Vo. 40, No. 3, (1994) pp. M728–M731.

Frano Fazzalari et al, "An Intrapleural Lung Prosthesis: Rationale, Design, and Testing," Artificial Organs, vol. 18, No. 11, (1994) pp. 801–805.

Cook et al, "Testing of an Intrathoracic Artificial Lung in a Pig Model," ASAIO Journal, vol. 42 (1996) pp. M604–M609.

William R. Lynch et al, "Hemodynamic Effect of Low–Resistance Artificial Lung in Series With the Native Lungs of Sheep," Ann. Thorc Surg, vol. 69 (2000) pp. 351–356.

*Primary Examiner*—Angela D. Sykes
*Assistant Examiner*—Leslie R Deak
(74) *Attorney, Agent, or Firm*—Brinks Hofer Gilson & Lione

(57) ABSTRACT

An apparatus for exchanging gases in a liquid is provided. Preferably, the apparatus comprises a housing, a first inlet, a gas exchange medium, a separator, a first outlet, and a second inlet and outlet. The apparatus may further comprise a circumferential collection gap that collects liquid from the gas exchange medium and directs it toward the first outlet. Also, the apparatus may further comprise a compliant chamber positioned near the first inlet. The compliant chamber reduces the overall impedance of the apparatus. The apparatus is particularly well-suited for use as an implantable, artificial lung. In this embodiment, the liquid comprises blood and the apparatus exchanges supplied oxygen for waste carbon dioxide.

30 Claims, 3 Drawing Sheets

U.S. PATENT DOCUMENTS

| | | |
|---|---|---|
| 5,817,278 A | 10/1998 | Fini et al. |
| 5,817,279 A | 10/1998 | Eilers et al. |
| 5,823,987 A | 10/1998 | Elgas et al. |
| 5,849,186 A | 12/1998 | Raneri et al. |
| 5,851,486 A | 12/1998 | Plotkin |
| 5,858,233 A | 1/1999 | Elgas et al. |
| 5,863,501 A | 1/1999 | Cosentino |
| 5,906,741 A | 5/1999 | Elgas et al. |
| 5,922,281 A | 7/1999 | Elgas et al. |
| 5,964,725 A | 10/1999 | Sato et al. |
| 6,001,306 A | 12/1999 | McFall et al. |
| 6,004,511 A | 12/1999 | Biscegli |
| 6,017,493 A | 1/2000 | Cambron et al. |
| RE36,774 E | 7/2000 | Cosentino et al. |
| 6,113,782 A | 9/2000 | Leonard |
| 6,117,390 A | 9/2000 | Corey, Jr. |
| 6,451,257 B1 * | 9/2002 | Flamer .................. 422/44 |

* cited by examiner

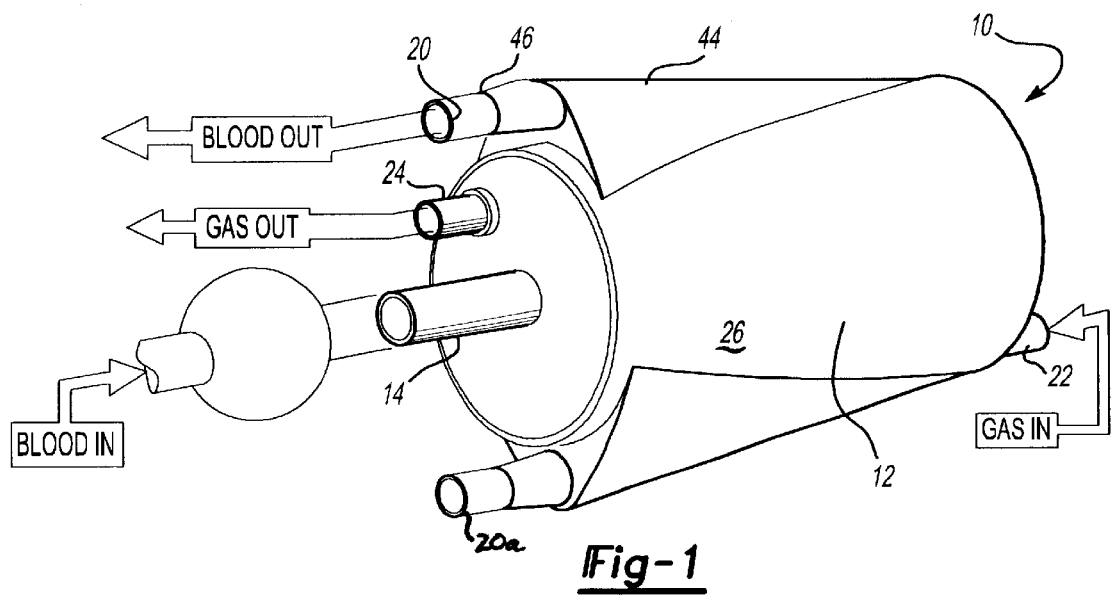
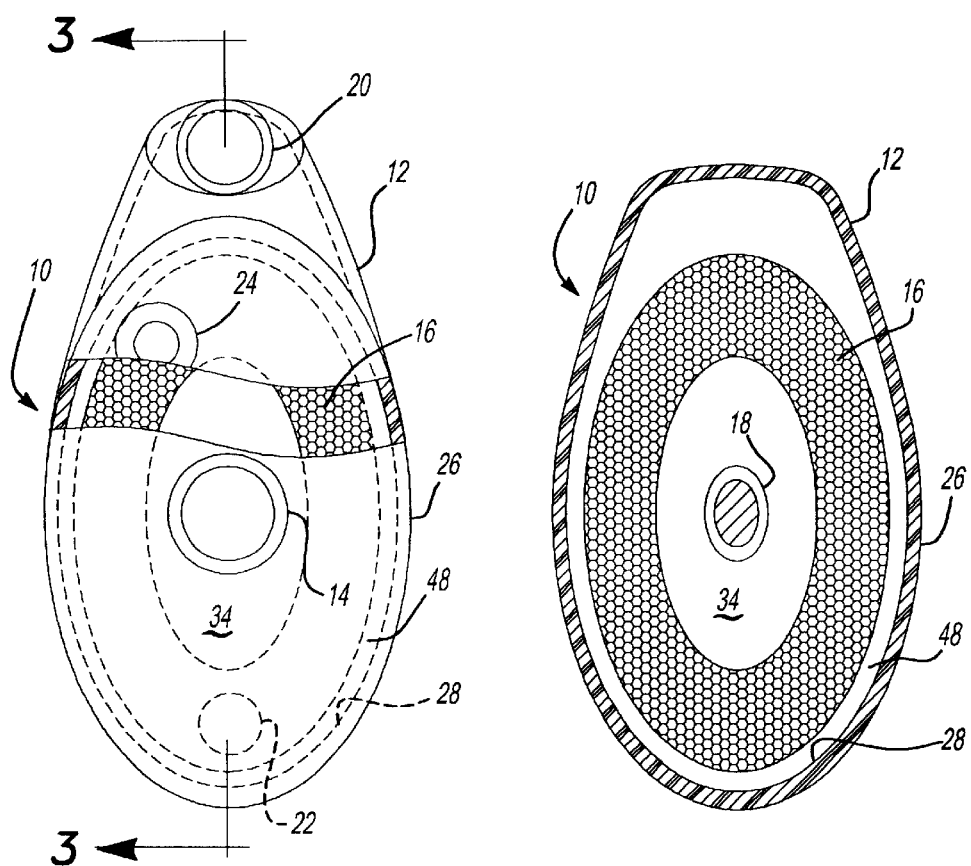
Fig-1
Fig-2  Fig-4

APPARATUS FOR EXCHANGING GASES IN A LIQUID

FEDERALLY SPONSORED RESEARCH OR DEVELOPMENT

This invention was made with support from the U.S. Government under Grant No. 1R43HL53168-02 and 1R42HL67523-02A1 awarded by the National Institutes of Health. The U.S. Government has certain rights in the invention.

FIELD OF THE INVENTION

The present invention relates to an apparatus that allows for the exchange of gases in a liquid sample. More specifically, the invention relates to a blood oxygenator, which allows external oxygen to be incorporated into a blood sample while carbon dioxide is removed from the sample.

The invention includes several features that make it particularly well suited for use as an artificial lung. Indeed, the apparatus according to the present invention has several characteristics that make it suitable for use in an extracorporeal bypass circuit, as well as a temporary in vivo replacement for a mammalian lung.

BACKGROUND OF THE INVENTION

Blood oxygenators are frequently used to accomplish the gas exchange functions normally performed by the lungs. Conventional blood oxygenators contain a gas exchange medium positioned adjacent a flowing stream of blood. When attached to an oxygen supply, the blood is perfused with oxygen and carbon dioxide is removed.

Typically, these devices are utilized when a patient's lungs are temporarily disabled. The situations in which a patient needs a blood oxygenator can generally be classified into two types: short term and indefinite term. Open heart surgery provides an example of a short-term need for a blood oxygenator. During this procedure, a patient's heart can be stopped temporarily. To continue vital functions of the circulatory system, an extracorporeal bypass circuit is constructed, in which a pump sends the patient's blood through a series of devices. A blood oxygenator is frequently included in these circuits so that the patient's blood can continue to deliver oxygen to the tissues of the body.

The prior art provides several examples of blood oxygenators that are suitable for use in these extracorporeal bypass circuits. Unfortunately, the use of these external circuits are not ideal for situations in which the need for an artificial blood oxygenator spans an indefinite term. The extracorporeal bypass circuits are bulky, labor intensive, and expensive to operate. For these reasons and more, these circuits are typically only used to manage the blood oxygenation needs of the indefinite term patient who requires long term intensive care.

Many indefinite term patients are those awaiting a lung transplantation procedure, which has become a well-established clinical procedure for several respiratory maladies, including chronic obstructive pulmonary disease, emphysema, cystic fibrosis, and idiopathic pulmonary fibrosis. Unfortunately, many patients who would benefit from a lung transplant must wait to receive a suitable lung. Furthermore, immunosuppressive therapy, which is commonly used prior to transplantation procedures, is generally a contraindication to extracorporeal support, such as by a bypass circuit, due to the risk of bacterial infections.

As a consequence, there is a need for a blood oxygenator that is suitable for use in indefinite term patients. A blood oxygenator that is able to provide gas exchange functions without imposing a significant load onto the heart would be particularly desirable. Furthermore, an implantable blood oxygenator, which could effectively serve as an artificial lung, would enhance the lifestyle of indefinite term patients and provide a bridge therapy to lung transplantation.

SUMMARY OF THE INVENTION

The present invention provides an apparatus that allows for exchange of gases in a liquid sample. In a particularly preferred embodiment, the invention provides a blood oxygenator. The blood oxygenator according to the present invention has several characteristics that make it suitable for use as an artificial lung in indefinite term patients.

In one embodiment, the apparatus according to the present invention comprises a housing having an inner surface, a first end and a second end. The housing defines an interior chamber that has inner and outer portions. A gas exchange medium is disposed in the outer portion of the interior chamber, and a separator is disposed in the inner portion. The separator preferably extends substantially along the length of the gas exchange medium.

The apparatus includes first and second inlets and first and second outlets.

The first inlet is adapted to introduce a stream of liquid into the interior chamber, on an axial path extending from the first end of the housing to the second end, and preferably directed toward the separator.

The first outlet allows the liquid to exit the apparatus after flowing through or past the gas exchange medium. In the application described in detail herein, the first inlet and outlet serve as a blood inlet and outlet.

The second inlet and second outlet are adapted to introduce and carry away, respectively, gas from the gas exchange medium. In the application described herein, the second inlet and outlet serve as an air or oxygen inlet and outlet.

The separator functions to radially divert the stream of liquid off its axial path and toward the gas exchange medium. Consequently, the liquid flows principally radially through the gas exchange medium.

The outer portion of the housing's chamber may further define a circumferential collection gap that collects liquid exiting from the gas exchange medium and directs it toward the first outlet.

Preferably, the housing and first outlet both have a generally elliptical cross-sectional shape. Particularly preferable, the ovoid shapes of these elements are oriented such that a major axis of the elliptical shape of one element is substantially perpendicular to a major axis of the elliptical shape of the other element.

The apparatus of the present invention may also include a compliant chamber placed on a communicative passageway that carries liquid to the first inlet. In a preferred embodiment, the complaint chamber comprises a relatively non-elastic chamber formed by the communicative passageway. One end of the chamber can be fixedly attached to a surface while another end remains adjustable. Alternatively, the compliant chamber can be formed of an elastic material. Also alternatively, the compliant chamber can be placed in a sealed container having a fluid that surrounds the chamber. Furthermore, one or more springs could be utilized to store energy and provide the desired compliance.

The apparatus may further comprise a means for warming and/or cooling the liquid being passed through the device. In one embodiment, a conductive element, such as electrical tape, is disposed on the separator. The electrical tape is responsive to an external temperature regulator and warms the liquid, such as blood, when an electrical current passes through the tape.

The present invention provides an apparatus with impedance characteristics that allow it to be incorporated into the circulation without placing a significant load on the right heart. Indeed, the impedance characteristics of the blood oxygenator according to the present invention allows for perfusion of the oxygenator by the native circulation without detrimental effects on the right ventricle.

BRIEF DESCRIPTION OF THE DRAWINGS

FIG. 1 is a perspective view of a blood oxygenator according to a first preferred embodiment of the present invention.

FIG. 2 is an end view, partially broken away, of the blood oxygenator illustrated in FIG. 1.

FIG. 4 is a cross-sectional view of the blood oxygenator taken along line 4,4 in FIG. 3.

DETAILED DESCRIPTION OF THE INVENTION

Figure 3:
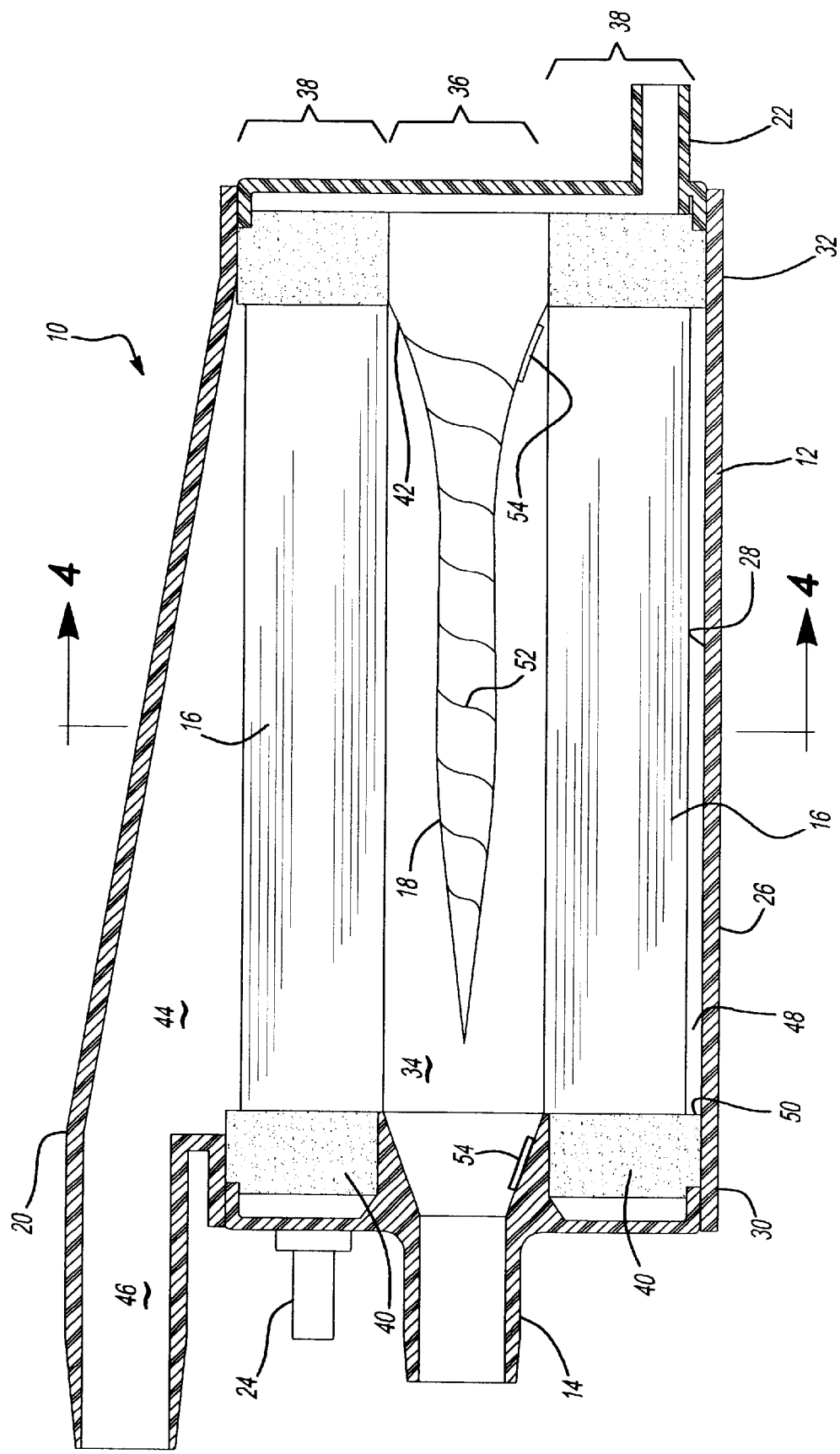
FIG. 3 is a cross-sectional view of the blood oxygenator taken along line 3,3 in FIG. 2.

The following description of preferred and alternate embodiments of the invention provides examples of the present invention. The embodiments discussed herein are merely exemplary in nature, and are not intended to limit the scope of the invention in any manner. Rather, the description of these preferred embodiments serves to enable a person of ordinary skill in the relevant art to make and use the present invention.

The present invention provides an apparatus for exchanging gases in a liquid. The apparatus is particularly well suited for use as a blood oxygenator. FIGS. 1 through 4 illustrate a blood oxygenator 10 in accordance with a first preferred embodiment of the present invention.

The blood oxygenator 10 comprises a housing 12, a first inlet 14, a gas exchange medium 16, a separator 18, a first outlet 20, a second inlet 22, and a second outlet 24.

The housing 12 comprises the main body of the oxygenator 10, and has an exterior surface 26, an inner surface 28, a first end 30, a second end 32, and a wall extending therebetween. The housing 12 defines an interior chamber 34 that provides the space in which gas exchange functions are performed.

As best illustrated in FIG. 2, the housing 12 preferably has an elliptical cross-sectional shape. The elliptical shape confers several benefits onto the oxygenator 10, including increased ease of handling and suitability for implanting into the thoracic cavity of a mammal, such as a human.

The housing 12 is preferably comprised of a rigid material, such as a plastic. The use of biocompatible materials known to those skilled in the art facilitates the use of the oxygenator 10 as an implanted artificial lung. A particularly preferred material for the housing 12 is polycarbonate.

The housing 12 defines the outermost surface of the oxygenator 10, and therefore dictates the size of the oxygenator 10. Preferably, the housing 12 is dimensioned such that the ratio of its major axis to its minor axis is between about 1 and 4. Particularly preferably, the ratio of major axis to minor axis is about 1.32. The inventors have found that a blood oxygenator according to the present invention that has a length of about 6.375" and a maximum height of about 4.219" facilitates implantation of the oxygenator.

As indicated above, the interior chamber 34 provides the necessary space for gas exchange to occur. As best illustrated in FIG. 2, the interior chamber 34 can be divided into two primary regions: an inner portion 36 and an outer portion 38. The inner portion 36 comprises the center of the chamber 34, while the outer portion 38 comprises the periphery of the chamber 34, i.e. the area of the chamber 34 that is adjacent the inner surface 28 of the housing 12. Since the inner 36 and outer 38 portions are regions of the interior chamber 34, there is no precise line that defines the regions.

As best illustrated in FIG. 3, the first inlet 14 comprises a communicative passageway that provides communication to the interior chamber 34 of the oxygenator 10. Preferably the first inlet 14 comprises a passageway that traverses the first end 30 of the housing 12 at a point that allows the first inlet 14 to provide direct access to the inner portion 36 of the interior chamber 34.

The first inlet 14 is preferably integrally formed by the housing 12. Alternatively, any suitable communicative passageway can be utilized. Furthermore, the first inlet 14 may define features that facilitate connection to another communicative passageway, such as a section of a plastic tubing or the like. Such features can include barbs, hooks, clamps, and any other suitable connection feature. Alternatively, the first inlet 14 can be adapted such that it can be directly attached, such as by sewing or other suitable means, to tubes or a vessel of the native circulatory system.

The gas exchange medium 16 provides the surface area necessary for the exchange of gases in the liquid to occur. Preferably, as best illustrated in FIG. 4, the gas exchange medium 16 is disposed in the outer portion 38 of the interior chamber 34, leaving the inner portion 36 free of the gas exchange medium 16. Also preferable, the gas exchange medium 16 is disposed completely around the inner portion 36 of the chamber 34.

The gas exchange medium 16 is adapted to carry a first gas, such as oxygen, in such a manner that allows the gas to be taken up by a liquid contacting the medium 16, such as blood. Further, the medium 16 is adapted to carry away any excess of the first gas, as well as any other gas given off by the liquid, such as carbon dioxide. Many examples of suitable gas exchange mediums are known in the art, and any can be employed in the present invention. The medium preferably comprises a plurality of individual hollow fibers, such as those discussed in U.S. Pat. Nos. 5,964,725 to Sato, et al. for a GAS EXCHANGE APPARATUS USING IMPROVED SILICONE RUBBER HOLLOW FIBER and 6,004,511 to Biscegli for a HOLLOW FIBER OXYGENATOR. Alternatively, the gas exchange medium 16 can comprise any suitable exchange medium known to those skilled in the art. A particularly preferred gas exchange medium comprises a two-dimensional mesh in which fibers along one dimension are hollow gas exchange fibers and fibers in the second dimension are connecting support fibers.

Preferably, as best illustrated in FIG. 3, the gas exchange medium 16 is seated within the housing 12. The seating of the medium 16 prevents movement of the medium 16 that may interfere with operation of the oxygenator 10, such as movement of the medium 16 toward or into the inner portion 36 of the interior chamber. Preferably, a section of potting material 40 is disposed at both the first 30 and second 32 ends of the oxygenator 10 and around the respective ends of the gas exchange medium 16. The potting material 40 is preferably positioned to separate the gas phase from the liquid phase within the oxygenator 10. Various potting materials are used in conventional blood oxygenators, and a variety or types will be known to those skilled in the art. U.S. Pat. No. 6,113,782 to Leonard for POTTING OF TUBULAR BUNDLES IN HOUSING provides an example of suitable potting material.

During operation, blood enters the oxygenator 10 through the first inlet 14 along an axial path extending from the first end 30 toward the second end 32. Because the gas exchange medium 16 is disposed around the inner portion 36 of the interior chamber 34, the liquid must be radially diverted so that it can encounter the medium 16. Accordingly, a separator 18 is employed. The separator 18 functions to radially divert the incoming stream of liquid off of its initial axial path and toward the gas exchange medium 16. Further, the separator 18 can function to prevent impingement of the liquid on the second end 32 of the oxygenator, or the potting material 40 disposed therein.

As illustrated in FIG. 3, the separator 18 is disposed in the inner portion 36 of the interior chamber 34 along the lengthwise axis of the housing 12. Preferably, the separator 18 comprises an element separate from the housing 12, and one end of the separator 18 is fixedly secured to the second end 32 of the housing 12, i.e., the end opposite the first inlet 14. This attachment can be direct to the housing 12, or alternatively, to the potting material 40, which is secured to the housing 12. Alternatively, the separator 18 can be integrally formed with the interior surface of the housing. Also preferable, the separator 18 extends substantially along the length of the gas exchange medium 16. Preferred lengths for the separator 18, as compared to the length of the gas exchange medium 16, are within the range of about 50% to about 99%. Particularly preferable, the separator 18 is between about 75% and 95% of the length of the medium 16. Most preferable, the separator 18 is approximately 90% as long as the gas exchange medium 16.

The separator 18 is preferably conical in shape. As illustrated in FIG. 3, the separator 18 is preferably positioned such that the tip of the conical form is substantially opposite the first inlet 14. Also preferable, the cross-sectional shape of the separator 18, at any position along its length, is generally elliptical. Furthermore, the separator 18 may define a tapered surface 42 at a point near the end secured to the housing 10. This tapered surface 42 prevents the incoming stream from impinging on the potting material 40 or inner surface 28 of the housing 10 at the second end 32, i.e., the end opposite the first inlet 14. This also lowers the pressure drop that occurs across the gas exchange medium 16. As illustrated in FIG. 3, the opposite end of the separator 18, i.e., the end near the first inlet 14, preferably draws to a point.

The overall shape of the separator functions to prevent significant pressure drop across the oxygenator 10. For example, the point near the first inlet 14 allows the separator 18 to radially divert incoming fluid while providing minimal resistance to flow. Also, the tapered surface 42 at the opposite end allows the separator 18 to effectively divert a flowing stream of liquid having less volume toward the gas exchange medium 16.

Being positioned within the housing 10, the separator 18 comes into contact with liquid flowing through the oxygenator 10 during operation. As indicated above, the liquid will frequently comprise blood, which contains numerous living cells. Accordingly, the separator 18 is preferably formed of a biocompatible material, such as biocompatible plastic. Particularly preferable, the separator 18 is fabricated from the same material as the housing 12.

The first outlet 20 comprises a communicative passageway that provides fluid communication between the interior chamber 34 of the oxygenator 10 and the external environment. For example, the first outlet 20 can be connected to the remainder of an extracorporeal bypass circuit, or to the pulmonary artery of a patient. In the flow path, the first outlet 20 is positioned after the gas exchange medium 16. Accordingly, the first outlet 20 functions to carry away liquid that has encountered the medium 16, i.e., liquid that has undergone gas exchange.

As best illustrated in FIG. 3, the first outlet 20 preferably comprises a collection portion 44 and an outlet portion 46. The collection portion 44 provides the opening that collects liquid from the gas exchange medium 16, and the outlet portion 46 provides the passageway that allows the liquid to exit the oxygenator 10. Preferably, the collection portion 44 comprises a tapered region having an opening that extends substantially along the length of the gas exchange medium 16. This allows for even collection of liquid from the medium 16 and helps to prevent pressure drop. The taper preferably proceeds from a narrow end located near the second end 32 of the housing 12, to an enlarged end located near the first end 30. Preferably, the taper proceeds at an angle of between approximately 5° and 20° from parallel to the lengthwise axis of the oxygenator 10. Particularly preferable, the taper proceeds at an angle of approximately 9.7° degrees from parallel to the lengthwise axis of the oxygenator 10. The enlarged end provides the transition, i.e., direct fluid communication, from the collection portion 44 to the outlet portion 46.

As best illustrated in FIG. 2, the collection portion 44 preferably has an elliptical cross-section shape. Particularly preferable, a major axis of the elliptical cross-sectional shape of the collection portion 44 is substantially perpendicular to a major axis of the elliptical cross-section shape of the housing 12.

As best illustrated in FIG. 1, the collection portion 44 preferably tapers such that the outlet portion 46 has a circular cross-sectional shape. The circular cross-sectional shape facilitates connection of the first outlet 20 to a communicative passageway that carries away exiting liquid, such as a vascular graft or a section of tubing.

Preferably, the first outlet 20 is integrally formed by the housing 12. Also preferable, the outlet portion 46 is substantially parallel to the first inlet 14. The first outlet 20, in a manner similar to that described above for the first inlet 14, is preferably adapted to facilitate connection to tubes or other passageways, or even to facilitate direct attachment, such as by sewing, to a vessel of the native circulatory system.

The oxygenator 10 may further include a third outlet 20a. As illustrated in FIG. 1, the third outlet 20a is preferably identical to the first outlet 20. The third outlet 20a is in fluid communication with the interior chamber 34. As shown in the figure, the third outlet 20a preferably has an identical form and configuration as the first outlet 20. Also preferable, the third outlet 20a is preferably positioned opposite the first outlet 20 in the housing 12, such that it is a mirror image of the first outlet 20. In this embodiment, a connector of some type, such as a Y-connector, can be used to join passageways extending from the first 20 and third 20a outlets into a common passageway.

The second inlet 22 and second outlet 24 provide fluid communication with the gas exchange medium. The second inlet 22 defines a communicative passageway that allows an external gas source, such as an oxygen reservoir, to introduce a gas into the medium 16. The second outlet 24 defines a communicative passageway that is able to carry away excess supplied gas and/or a waste gas, such as carbon dioxide, from the medium 16.

Preferably, both the second inlet 22 and second outlet 24 are integrally formed by the housing 12. Also preferable, both the second inlet 22 and second outlet 24 define structural features, as described above for the first inlet 14 that facilitate connection to external communicative passageways, such as tubing and the like.

As best illustrated in FIG. 3, a clearance 48 preferably exists between the inner surface 28 of the housing 12 and the gas exchange medium 16. The clearance 48 is preferably formed by leaving a shoulder 50 in the potting material 40, near the inner surface 28 of the housing, that does not seat any portion of the gas exchange medium 16. This creates the clearance 48 between the medium 16 and the inner surface 28. Alternatively, the housing 12 can define a series of shoulders, recesses, and/or other structural features to form the clearance 48.

Preferably, as best illustrated in FIG. 4, the clearance 48 forms a circumferential gap that extends around the inner surface 28 of the housing 12. The gap 48 is preferably between about 0.05" and 0.25", and preferably uniform around the inner surface 28 of the housing. Particularly preferable, the gap 48 is about 0.10".

As best illustrated in FIG. 3, the clearance 48 preferably merges into the collection portion 44 of the first outlet 20. Thus, the clearance 48 is in fluid communication with the first outlet 20. This allows the clearance 48 to collect liquid that has passed through the gas exchange medium 16 and direct it into the first outlet 20.

The oxygenator 10 may also contain a heater that is adapted to warm blood or another liquid that enters the device. A variety of suitable heaters are known in the art and any can be used. Examples of suitable heaters include heat exchange tubes positioned proximate the gas exchange fibers and a conductive element disposed on a surface of the oxygenator 10. FIG. 3 illustrates an example of a conductive element used as a heater. In this embodiment, an electrical tape 52 is disposed on the separator 18, thereby being positioned to contact blood entering the oxygenator 10. The electrical tape 52 warms when a current is passed through it, thereby enabling it to warm the blood. Preferably, the electrical tape 52 is responsive to an external temperature regulator or an internal temperature sensor.

The oxygenator 10 may further include one or more sensors 54. The sensor(s) 54 can comprise any sensor adapted to measure various characteristics of the liquid being passed through the oxygenaotr 10. For example, when the oxygenator 10 is used to oxygenate blood, the sensor(s) 54 can include sensors adapted to measure $O_2$ concentration in the blood, $CO_2$ concentration in the blood, pressure flow, flow rate through the first 14 and/or second 22 inlets, temperature of the blood, pH of the blood, and hemoglobin concentration in the blood. Preferably, the sensor(s) 54 is adapted to provide an output signal to an external device such as a computer and/or printer. Various sensors in accordance with these preferred characteristics are known in the art and will not be described in detail herein.

Figure 5:
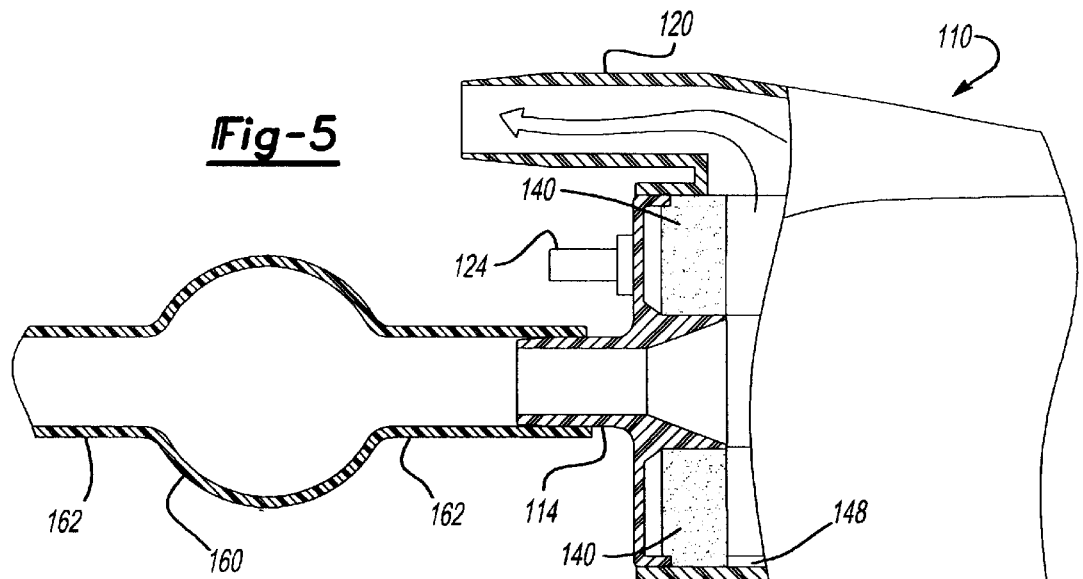
FIG. 5 is a partial cross-sectional view of a blood oxygenator according to a second preferred embodiment of the present invention and illustrates the use of a compliant chamber in the oxygenator.

FIG. 5 illustrates a blood oxygenator 110 according to a second preferred embodiment of the invention. This embodiment is similar to the first preferred embodiment, except as described below. Accordingly, like reference numbers in FIG. 5 refer to similar features and/or components illustrated in FIGS. 1, 2, 3 and 4.

In this embodiment, the oxygenator 110 includes a compliant chamber 160 located near the first inlet 114. The compliant chamber 160 allows the oxygenator 110 to receive the ejection volume of the right ventricle of the heart without placing a significant load on the right ventricle. The compliant chamber 160 allows for a change in volume when pressure is changed, thereby lowering overall impedance of the oxygenator 110. The inventors have discovered that the ability of the compliant chamber 160 to dampen impedance harmonics increases as the chamber is moved closer to the right heart.

The compliant chamber 160 is preferably disposed proximate the first inlet 114. Preferably, as illustrated in FIG. 5, the compliant chamber 160 is positioned in line with a communicative passageway 162 that ultimately connects to the first inlet 114. The communicative passageway 162 can be a vascular graft, tubing, or any other suitable passageway. Alternatively, the compliant chamber can be placed within the housing.

Preferably, the compliant chamber 160 defines an enlarged region in the passageway 162. In this embodiment, the chamber 160 can be a bulbous or other shaped region that is integrally formed in the passageway 162. Preferably, the chamber 160 comprises a relatively non-elastic material, such as polyurethane or a silicone-polyurethane copolymer. When secured for use with the oxygenator 110, the chamber 160 is preferably slightly elongated such that it is slightly deformed. The chamber 160 is then able to passively fill with the ejection volume of the right ventricle. (approximately 60–70 cc for human hearts).

Alternatively, the communicative passageway can comprise a flexible tubing, such as a segment of silicone or silicone-urethane copolymer tubing. The passageway forms the compliant chamber when the passageway receives fluid. The flexible nature of the passageway allows the passageway to expand upon receiving liquid, thereby forming the compliant chamber. Upon filling, the compliant chamber elastically recoils and propels the liquid into the first inlet of the oxygenator 110.

Figure 6:
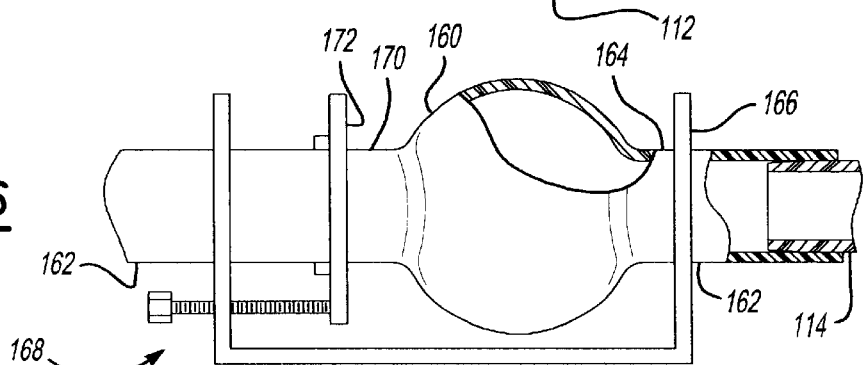
FIG. 6 is a cross-sectional view, partially broken away, of a second preferred embodiment of a compliant chamber in the blood oxygenator.

As illustrated in FIG. 6, one end 164 of the chamber 160 can be fixedly attached to a surface 166, such as a support brace 168. In this embodiment, another end 170 of the chamber 160 is attached to an adjustable surface 172 of the brace 168. This allows the length of the chamber 160 to be adjusted, which allows for the adjustment of the compliance of the chamber 160.

Figure 7:
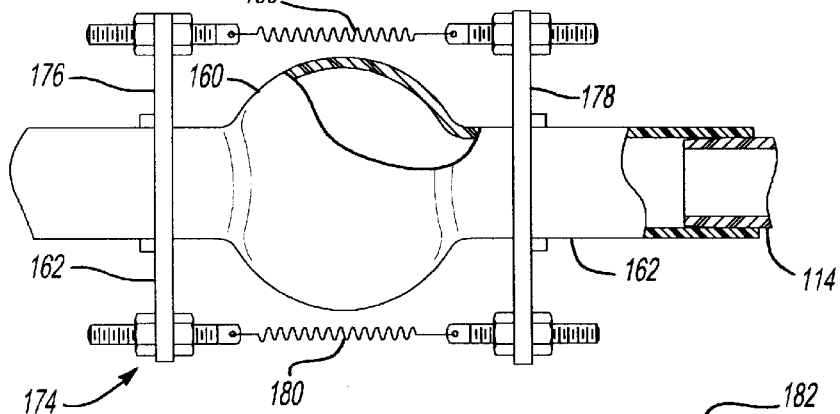
FIG. 7 is a cross-sectional view, partially broken away, of a third preferred embodiment of a compliant chamber in the blood oxygenator.

FIG. 7 illustrates an alternate brace 174 for use with the chamber 160. In this embodiment, the brace includes two surfaces 176,178 for securing two opposing ends of the chamber 160. Springs 180 are disposed between the surfaces 176,178 such that the surfaces 176,178 are connected to each other. The springs 180 are preferably enclosed or covered to facilitate implantation. Also, the springs 180 are preferably adjustable, and serve to allow for adjustment of compliance of the chamber 160.

Figure 8:
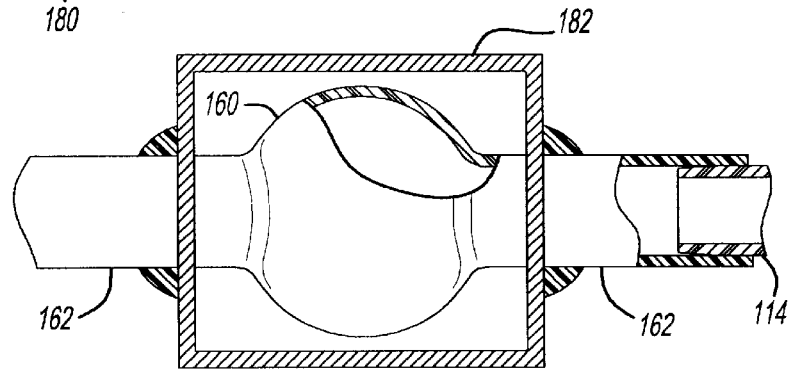
FIG. 8 is a cross-sectional view, partially broken away, of a fourth preferred embodiment of a compliant chamber in the blood oxygenator.

As illustrated in FIG. 8, the compliant chamber 160 can be positioned within a sealed rigid container 182. In this embodiment, a fluid, such as a gas or liquid, is placed within the sealed container 182 and around the compliant chamber 160. This allows the compliance of the chamber 160 to be regulated by the pressure of the fluid in the container 182.

The present invention also provides a method of operating a blood oxygenator. The method is particularly well suited for operating a blood oxygenator that has a housing defining an interior chamber, a blood inlet in fluid communication with an inner portion of the interior chamber, a gas exchange medium disposed in an outer portion of the interior chamber, a blood outlet in fluid communication with the gas exchange medium and a gas inlet and outlet in fluid communication with the gas exchange medium.

The method preferably comprises introducing blood into the inner portion of the interior chamber by passing the blood through the blood inlet along an axial path that extends substantially from one end of the oxygenator to the opposite end, radially diverting the blood toward the outer portion of the interior chamber such that the blood passes through the gas exchange medium, and directing the blood through the blood outlet such that it exits the oxygenator. The radially diverting the blood is preferably accomplished by utilizing a separator in the interior chamber of the oxygenator, as described above.

In order to facilitate gas exchange, the method preferably further comprises introducing a gas, such as oxygen or air, into the gas inlet such that it passes through the gas exchange medium and exits the oxygenator through the gas outlet.

It will be readily understood that, while the invention has been described herein as being particularly well suited for oxygenating blood, in which the liquid comprises blood and the gas comprises oxygen or air, the invention can also be used in any other application in which it is desired to introduce a gas into a liquid. For example, various anesthetics can be delivered into the device in order to introduce the anesthetic into a patient's blood.

All references cited herein, except to the extent they contradict any statement or definition made herein, are herby incorporated into this disclosure in their entirety.

The foregoing disclosure includes the best mode devised by the inventors for practicing the invention. It is apparent, however, that several variations in accordance with the present invention may be conceivable to one of ordinary skill in the relevant art. Inasmuch as the foregoing disclosure is intended to enable such person to practice the instant invention, it should not be construed to be limited thereby, but should be construed to include such aforementioned variations and should be limited only by the spirit and scope of the following claims.

We claim:

1. An apparatus for exchanging gases in a liquid, comprising:
   a housing having a first end, a second end, an inner surface, and defining an interior chamber;
   a first inlet in fluid communication with the interior chamber and positioned to introduce said liquid into the interior chamber substantially along an axial path extending from the first end toward the second end;
   a gas exchange medium disposed in the interior chamber;
   a conical separator disposed in an inner portion of the interior chamber, the separator extending substantially along the length of the gas exchange medium and configured for diverting a stream of said liquid radially outward toward the gas exchange medium substantially along the length of the gas exchange medium;
   a first outlet in fluid communication with the interior chamber;
   a second inlet in fluid communication with the gas exchange medium; and
   a second outlet in fluid communication with the gas exchange medium.

2. An apparatus in accordance with claim 1, wherein a clearance exists between the gas exchange medium and the inner surface of the housing.

3. An apparatus in accordance with claim 1, wherein the clearance comprises a circumferential collection gap between the inner surface and the gas exchange medium.

4. An apparatus in accordance with claim 3, wherein the circumferential gap extends substantially along the length of the gas exchange medium.

5. An apparatus in accordance with claim 1, wherein the separator is spaced from the gas exchange medium.

6. An apparatus in accordance with claim 1, wherein an end of the separator is fixedly attached to the housing.

7. An apparatus in accordance with claim 1, wherein the gas exchange medium comprises a plurality of gas exchange fibers.

8. An apparatus in accordance with claim 7, further comprising potting material disposed at the first and second ends of the housing, wherein the gas exchange fibers are seated in the potting material.

9. An apparatus in accordance with claim 1, wherein the first outlet comprises a collection portion and an outlet portion, and wherein the collection portion extends substantially along the length of the gas exchange medium.

10. An apparatus in accordance with claim 9, wherein the collection portion has a narrow end and an enlarged end, and wherein the enlarged end directly communicates with the outlet portion.

11. An apparatus in accordance with claim 9, wherein the collection portion has a generally elliptical cross-sectional shape and the outlet portion has a generally circular cross-sectional shape.

12. An apparatus in accordance with claim 1, wherein the housing has a generally elliptical shape.

13. An apparatus in accordance with claim 12, wherein the first outlet has a generally ovoid shape.

14. An apparatus in accordance with claim 13, wherein a major axis of the elliptical shape of the housing is substantially perpendicular to a major axis of the elliptical shape of the first outlet.

15. An apparatus in accordance with claim 1, further comprising a communicative passageway connected to the first inlet and adapted to carry said liquid to the first inlet, and a compliant chamber disposed on the communicative passageway.

16. An apparatus in accordance with claim 15, wherein the compliant chamber comprises a chamber formed by the communicative passageway and adapted to passively fill with said liquid.

17. An apparatus in accordance with claim 15, wherein one end of the compliant chamber is fixedly attached to the first inlet.

18. An apparatus in accordance with claim 15, wherein the compliant chamber is comprised of an elastic material.

19. An apparatus in accordance with claim 15, further comprising a rigid container disposed about the compliant chamber.

20. An apparatus in accordance with claim 19, wherein the rigid container is sealed and contains a fluid disposed about the compliant chamber.

21. An apparatus in accordance with claim 1, further comprising a third outlet in fluid communication with the interior chamber.

22. An apparatus in accordance with claim 21, wherein the third outlet is positioned opposite the first outlet.

23. An apparatus in accordance with claim 21, wherein the third outlet is a mirror image of the first outlet.

24. An apparatus in accordance with claim 1, further comprising a sensor adapted to measure a characteristic of said liquid while within said apparatus.

25. An apparatus for exchanging gases in a liquid, comprising:
- a housing having an inner surface, a first end, and a second end, and defining an interior chamber having inner and outer portions;
- a first inlet in fluid communication with the inner portion of the interior chamber;
- a gas exchange medium disposed in the outer portion of the interior chamber;
- a first outlet in fluid communication with the outer portion of the interior chamber;
- a second inlet in fluid communication with the gas exchange medium; and
- a second outlet in fluid communication with the gas exchange medium;
- a conical separator and disposed substantially opposite the first inlet and configured for radially diverting said liquid entering the interior chamber toward the gas exchange medium substantially along the length of the gas exchange medium.

26. An apparatus in accordance with claim 25, further comprising a heater adapted to change the temperature of said liquid.

27. An apparatus for exchanging gases in a liquid comprising:
- a housing having an inner surface, a first end, and a second end, and defining an interior chamber having inner and outer portions;
- a first inlet in fluid communication with the interior chamber and positioned to introduce a stream of said liquid into the interior chamber substantially along an axial path extending from the first end to the second end;
- a gas exchange medium disposed in the outer portion of the interior chamber such that a clearance exists between the gas exchange medium and the inner surface of the housing;
- a conical separator disposed in the inner portion of the interior chamber, the separator extending substantially along the length of the gas exchange medium and configured for diverting a stream of said liquid entering the interior chamber through the first inlet in a radial direction toward the gas exchange medium substantially along the length of the gas exchange medium;
- a first outlet in fluid communication with the interior chamber;
- a second inlet in fluid communication with the gas exchange medium; and
- a second outlet in fluid communication with the gas exchange medium.

28. An apparatus in accordance with claim 27, wherein the clearance forms a circumferential gap between the inner surface of the housing and the gas exchange medium.

29. An apparatus in accordance with claim 28, wherein the clearance merges with the first outlet.

30. An apparatus for exchanging gases in a liquid, comprising:
- a housing having an inner surface, a first end, and a second end, and defining an interior chamber having inner and outer portions;
- a first inlet in fluid communication with the inner portion of the interior chamber;
- a gas exchange medium disposed in the outer portion of the interior chamber;
- a first outlet in fluid communication with the outer portion of the interior chamber;
- a second inlet in fluid communication with the gas exchange medium; and
- a second outlet in fluid communication with the gas exchange medium;
- a separator defining a generally conical shape and disposed substantially opposite the first inlet and configured for radially diverting entering the interior chamber toward the gas exchange medium substantially along the length of the gas exchange medium; and a heater configured for changing the temperature of said liquid wherein the heater comprises a conductive element disposed on the separator and adapted to warm said liquid when an electrical current is passed through the conductive element.

* * * * *